United States Patent [19]

Everson

[11] Patent Number: 4,628,914

[45] Date of Patent: Dec. 16, 1986

[54] THERAPEUTIC MALE GENITAL APPLIANCE

[76] Inventor: Carl E. Everson, 181 Wyleswood Dr., Berea, Ohio 44017

[21] Appl. No.: 813,850

[22] Filed: Dec. 27, 1985

[51] Int. Cl.⁴ ............................................. A61F 5/00
[52] U.S. Cl. ..................................... 128/79; 128/327
[58] Field of Search ............... 128/79, 327, DIG. 25

[56] References Cited

U.S. PATENT DOCUMENTS

| | | | |
|---|---|---|---|
| 1,073,524 | 9/1913 | Russell | 128/79 |
| 1,073,525 | 9/1913 | Russell | 128/79 |
| 1,221,518 | 4/1917 | Dygert | 128/79 |

FOREIGN PATENT DOCUMENTS

| | | | |
|---|---|---|---|
| 319261 | 3/1920 | Fed. Rep. of Germany | 128/327 |
| 615801 | 7/1935 | Fed. Rep. of Germany | 128/327 |
| 858288 | 7/1949 | Fed. Rep. of Germany | 128/79 |

Primary Examiner—Gene Mancene
Assistant Examiner—Cary E. Stone
Attorney, Agent, or Firm—Donald A. Bergquist

[57] ABSTRACT

This invention relates to a device for providing therapeutic support to the penis of a man who suffers either partial or total sexual impotence, which device thereby allows nearly normal sexual activity between him and his partner. The device comprises parts that are mounted on spring-loaded hinges that create external pressures on the corpora cavernosa, the erectile tissues within the penis, compressing them so less blood is required to achieve erection and/or maintain the penis in an erect state. A significant feature of this invention is that it can be applied to or removed from the penis after coitus has begun and without complete disengagement of the male organ from the female.

12 Claims, 2 Drawing Figures

THERAPEUTIC MALE GENITAL APPLIANCE

BACKGROUND OF THE INVENTION

1. Field of the Invention

This invention relates to a device for providing therapeutic support to the penis of a man who suffers either partial or total sexual impotence, which device thereby allows nearly normal sexual activity between him and his partner.

The underlying causes of impotence are manyfold and may be either psychological in nature or physiological, such as advancing age. To the extent that such impotence may be curable, it is recognized that it may be preferable to treat the causal malady directly; however, even where this is possible, medical or psychological treatment frequently requires long periods of time to effect a cure. An effective device that is capable of assisting the male in his sexual function is therefore highly desirable.

2. Prior Art

Numerous U.S. patents are directed to this field of human activity and many specifically address the problem of sexual impotence in the male by the application of external means, as opposed to the use of surgically implanted means. Two principal physiological modes of operation are indicated in the prior art: firstly, physical support as in the use of one or more splints or an encircling substantially cylindrical support which may be split longitudinally to allow for expansion of the penis or for purposes of size adjustment or ease of applying or removing the device; secondly, the application of external pressure to the superficial dorsal vein or veins of the penis to restrict blood flow from the penis and spcifically from the corpora cavernosa, the erectile tissue within the penis. A combination of these modes is also anticipated by the prior art.

U.S. patents for devices wherein the desired effect is generated by the former mode are: U.S. Pat. Nos. 1,206,324; 1,383,944; 3,401,687; and 3,939,827.

U.S. patents for devices wherein the desired effect is generated by the latter mode are: U.S. Pat. Nos. 2,818,855; 3,511,230; 3,612,047; 3,636,948; 3,794,020; 4,203,432; and 2,581,114.

A combination of these two modes is present in U.S. Pat. No. 3,455,301.

Most of the devices described in the patents mentioned above suffer the decided disadvantage of having an element that must be applied by passing over the end of the penis. In the case of U.S. Pat. No. 3,455,301, the entire device is an endless ring. Even in cases wherein the cylindrical device is totally split lengthwise, as in U.S. Pat. Nos. 1,206,324, 1,383,944, and 3,401,687, which split might allow applying the device to a partially engaged penis, and endless band or tubular cover is necessary for use and must, by its endless nature, be passed over the exposed end of the penis. Thus, none of these devices can be applied after coitus has begun and without complete removal of the male organ from the female. These devices would be of only marginal benefit to the male who is able to attain an initially erect penis, sufficient to initiate coitus, but who cannot maintain his erection to achieve fulfilment of the sex act for the gratification of himself, his partner, or both of them.

Devices that do not require access to the end of the penis for applying them for use are described in U.S. Pat. Nos. 3,511,230, 3,612,047, 3,636,948, 3,794,020, 4,203,432, and 2,581,114. All of the devices of these patents are of the type that compress the superficial dorsal vein and offer little, if any, mechanical support of the penis or compression of the corpora cavernosa.

SUMMARY OF THE INVENTION

It is an object of the present invention to provide an improved therapeutic appliance that aids in sustaining a man's penis in an erect state for initiating and especially for cosummating coitus.

It is a further object of the present invention to provide such an appliance that may be removed or, more importantly, applied without full disengagement of the male organ from the female.

It is a further object of the present invention to provide such an appliance that functions primarily by compression of or restricting the expansion of a significant portion of the corpora cavernosa, the erectile tissues within the penis.

It is a further object of the present invention to provide such an appliance that functions secondarily by restricting the blood flow from the penis via the superficial dorsal vein or veins of the penis by means of the applied pressure.

It is a further object of the present invention to provide such an appliance that functions tertiarily by mechanical support of a portion of the shaft of the penis, especially near its base.

DETAILED DESCRIPTION OF THE INVENTION

Figure 1:
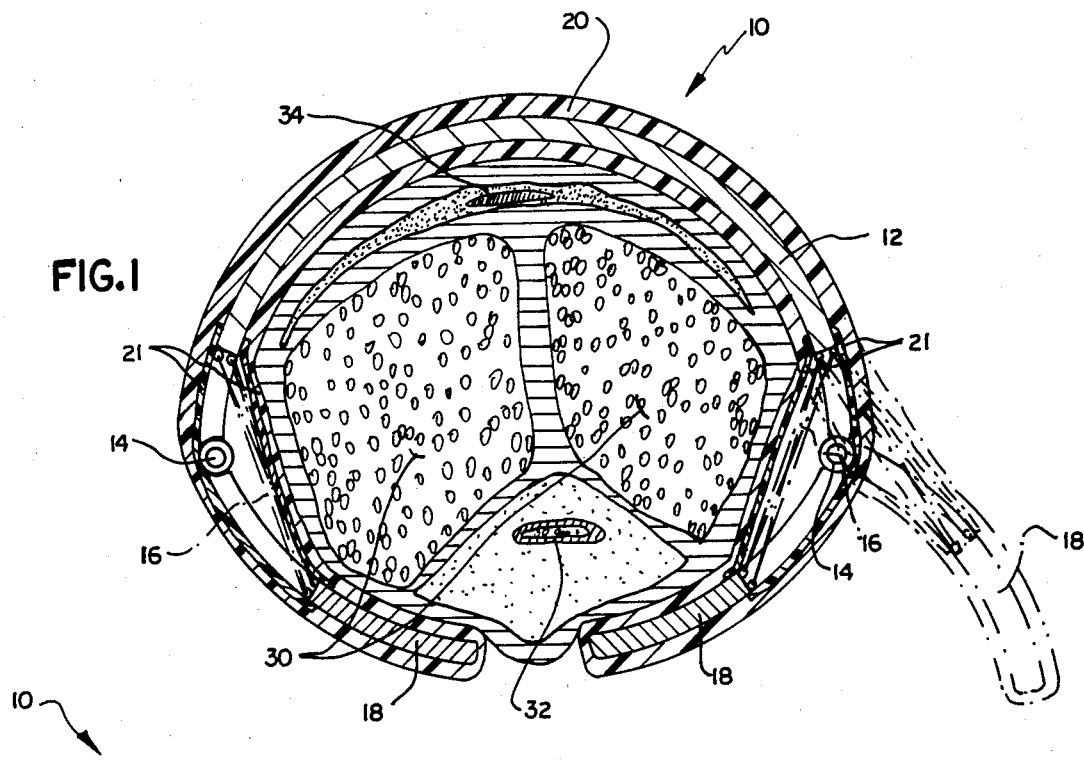
FIG. 1 shows, in cross sectional view, the appliance of this invention applied to a penis as viewed along the longitudinal axis.

This invention will best be understood by referring to the drawings, especially to FIG. 1. The invention is a therapeutic appliance 10 for the penis of a man comprising a rigid or semi-rigid substantially semicylindrically curved plate section 12 to which are attached by spring-loaded hinges, which hinges comprise a pivotal axis 14 and springs 16, two additional rigid or semi-rigid curved plate sections cylinders 18 or two additional rigid or semi-rigid sections of flat plates, which additional sections operate cooperatively with the curved plate section 12 to substantially but not completely enclose at least a portion of the length of the shaft of the penis. The pivotal axis may comprise common hinges with hinge pins or it may comprise a thin web or strip of flexible material such as a so-called "living hinge" in molded plastic articles or it may comprise other hinge means as may be found desirable in this use. Thus, by this hinge mechanism it can be seen that significant feature of this invention is that it can be applied to or removed from the penis after coitus has begun and without complete disengagement of the male organ from the female.

The function of the invention is illustrated in schematic cross-sectional form in FIG. 1 wherein the appliance is shown applied to a penis. The curved plate section 12 of the appliance covers the dorsal surface of the penis beneath which surface lies the superficial dorsal vein 34 or veins. As the appliance is applied to the penis, the sections 18 are open, and are held in the open position by the relationship between the pivotal axis 14 and the springs 16. The entire appliance is coated with a smooth, waterproof, resilient coating 20 of latex rubber, silicone rubber, or other such material. In applying such a coating, preferably by a dipping process followed by drying or curing the coating, a tape or film 21 must first be applied to cover the springs and/or hinges to prevent the coating, when it is in liquid form, from penetrating these working parts and thus preventing them from performing their essential functions. Preferably, this tape or film has adhesive on its edges only.

Figure 2:
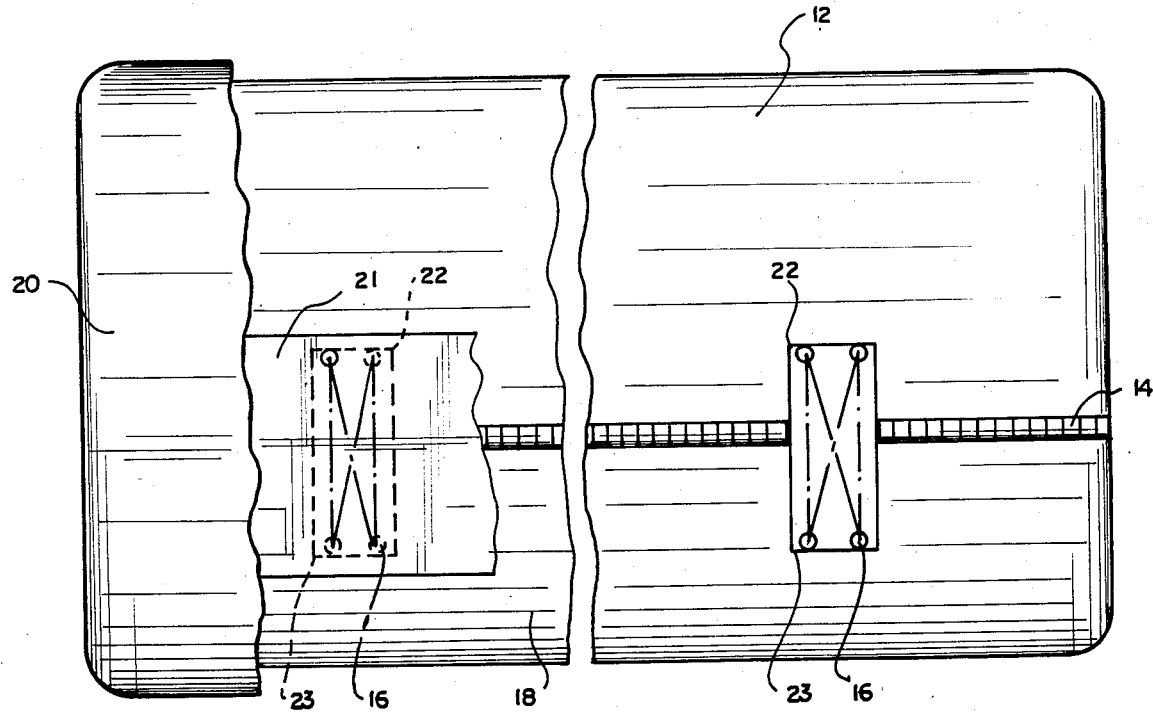
FIG. 2 shows a side view of the appliance in partial cutaway style.

In the case of the use of coil springs as shown in the figures, cutouts are made in both the first curved plate section and the additional sections as shown in FIG. 2 at 22 and 23. Thus, in the preferred mode, the springs are capable of holding the appliance in the open position for convenience in applying it to the penis and in the closed position for use thereof.

It is contemplated that the use of a C-shaped clip of spring steel might be used as a spring for the appliance and by its shape it would eliminate the need for the cutouts shown in the figures. Coil springs have been shown only to illustrate the operating principle in the simplest mode, but it should be understood that any suitable spring means, many of which may be applicable, may be used.

It will be clear to the reader that this appliance must be produced in a variety of sizes, both in diameter and in length, to properly deliver the desired therapeutic result to the end user. By way of defining the range of size that seems appropriate for this invention, the principal dimensions of concern are the diameter or average diameter of the substantially semicylindrically curved plate section and the length of the appliance. The diameter of this semi-cylindrical section should be approximately equal to the largest dimension of the user's flaccid penis, as measured near the base thereof and usually measured laterally across the penis, but this diameter may also be affected by the user's personal preference and comfort. The length of the appliance may vary considerably as it will depend upon the physical size of the penis of the user, his personal preference, and the desired therapeutic effect. To achieve the minimum therapeutic effect, the appliance should be selected that has a length equal or greater than 30% of the length of the shaft portion of the penis as measured from its base near the pubic bone to the base of the glans penis. In the preferred mode, this length will be equal to or greater than 50% of the shaft length so measured. The ultimate maximum length will be equal to 100% of the shaft length so measured, but in the preferred mode the maximum length is 80% of the shaft length.

The principal function of the appliance is to apply compressive forces or forces to restrict expansion to a significant area of the surfaces of the penis beneath which lie the corpora cavernosa 30, the erectile tissues within the penis, compressing them or restricting their expansion so less blood is required to achieve erection and/or maintain the penis in an erect state. The appliance does not, however, apply any local pressure to the urethra 32, which lies beneath the surface of the ventral portion of the penis. This feature is important because it is through the urethra that seminal fluid must pass during ejaculation in coitus; it is not the intent of this invention to hinder the function of the urethra in any manner whatsoever—its purpose is neither contraception nor the treatment of urinary incontinence.

A secondary function of this appliance is to cause external pressure on the dorsal surface of the penis to partially close the superficial dorsal vein or veins, thereby to reduce the blood flow from the corpora cavernosa; from the prior art, such blood flow reduction is known to promote and maintain penile erection. This external pressure arises as a reactive force that is the result of the opposite forces applied by the spring-loaded hinged sections 18.

A tertiary function of this appliance is to provide simple mechanical support to the penis while avoiding local pressure on the urethra of the penis and thereby to contribute to the completing of coitus by a man who may otherwise be unable to do so because of a lack of rigidity, regardless of the underlying reason therefor.

Now, having presented description and specific examples of my invention by way of explanation so one skilled in this art may reproduce the product of my invention, it should be understood that the invention has greater breadth than one can delineate in a few specific examples and it is my wish and intention to include in my invention the extent of the art that may be immediately obvious from my descriptions and examples; such breadth is included in the claims attached hereto.

I claim:

1. A therapeutic appliance for the penis of a man comprising a substantially semicylindrically curved plate section characterized as having a rigidity ranging from semi-rigid to rigid to which are attached by spring-loaded hinge means two additional plate sections characterized as having a rigidity ranging from semi-rigid to rigid, which additional sections operate cooperatively with the curved plate section to form a hollow cylinder to substantially but not completely enclose at least a portion of the length of the shaft of the penis.

2. An appliance as described in claim 1, wherein the said spring-loaded hinge means can alternately maintain the appliance in an open condition or in a closed condition for use thereof.

3. An appliance as described in claim 1 or 2, wherein during use thereof said additional sections, operating cooperatively with the semicylindrically curved plate section through the spring-loaded hinge means, apply compressive forces to a significant area of the surfaces of the penis beneath which lie the corpora cavernosa, without enclosing or applying a local pressure to the ventral surface of the penis beneath which lies the urethra.

4. An appliance as described in claim 3, wherein a therapeutic function derives from the fact that said compressive forces result in compression of a significant volume of the corpora cavernosa so as to require less blood to fill said corpora cavernosa, and thereby to maintain the penis in an erect condition.

5. An appliance as described in claim 3, wherein a therapeutic function derives from the fact that the reactive forces of the semicylindrically curved plate section, which forces are caused by the compressing of the penis by the hinged sections, acting upon the dorsal surface of the penis, result in partial closing of the superficial dorsal vein or veins, thereby reducing the blood flow from the corpora cavernosa, which blood flow reduction is known to promote and maintain penile erection.

6. An appliance as described in claim 3, wherein a therapeutic function is to enable the completing of coitus by offering mechanical support to the penis while avoiding local pressure on the urethra of the penis.

7. An appliance as described in claim 1 or 2, wherein during use thereof said additional sections, operating cooperatively with the semicylindrically curved plate section through the spring-loaded hinge means, and the semicylindrically curved plate section itself, apply restrictive forces to a significant area of the surfaces of the penis beneath which lie the corpora cavernosa, without enclosing or applying a local pressure to the ventral surface of the penis beneath which lies the urethra.

8. An appliance as described in claim 7, wherein a therapeutic function derives from the fact that said restrictive forces prevent the expansion of a significant volume of the corpora cavernosa so as to require less blood to fill said corpora cavernosa, and thereby to maintain the penis in an erect condition.

9. An appliance as described in claim 7, wherein a therapeutic function derives from the fact that the reactive forces of the semicylindrically curved plate section, which forces are caused by the restricting of the penis by the hinged sections, acting upon the dorsal surface of the penis, result in partial closing of the superficial dorsal vein or veins, thereby reducing the blood flow from the corpora cavernosa, which blood flow reduction is known to promote and maintain penile erection.

10. An appliance as described in claim 7, wherein a therapeutic function is to enable the completing of coitus by offering mechanical support to the penis while avoiding local pressure on the urethra of the penis.

11. An appliance as described in claim 1, wherein the said additional plate sections are curved.

12. An appliance as described in claim 1, wherein the said additional plate sections are flat.

* * * * *